United States Patent [19]

Kranz et al.

[11] 4,386,088

[45] * May 31, 1983

[54] COMBATING FUNGI WITH α-AZOLYL-KETO DERIVATIVES

[75] Inventors: Eckart Kranz; Wolfgang Krämer; Karl H. Büchel, all of Wuppertal; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[*] Notice: The portion of the term of this patent subsequent to Sep. 22, 1998, has been disclaimed.

[21] Appl. No.: 304,128

[22] Filed: Sep. 21, 1981

Related U.S. Application Data

[62] Division of Ser. No. 54,067, Jul. 2, 1979, Pat. No. 4,316,932.

[30] Foreign Application Priority Data

Jul. 21, 1978 [DE] Fed. Rep. of Germany ....... 2832234

[51] Int. Cl.³ .................... A01N 43/50; A01N 43/82; C07D 233/60; C07D 249/08
[52] U.S. Cl. .................................. 424/245; 424/232; 424/269; 424/273 R; 548/101; 548/262; 548/341
[58] Field of Search .................. 548/101, 262, 341; 424/245, 232, 269, 273 R

[56] References Cited

U.S. PATENT DOCUMENTS

| | | | |
|---|---|---|---|
| 4,102,891 | 7/1978 | Timmler et al. | 424/269 |
| 4,124,369 | 11/1978 | Kramer et al. | 548/262 |
| 4,154,842 | 5/1979 | Kramer et al. | 548/262 |
| 4,217,129 | 8/1980 | Shephard et al. | 548/262 |
| 4,291,047 | 9/1981 | Kranz et al. | 424/269 |
| 4,316,932 | 2/1982 | Kranz et al. | 548/341 |

FOREIGN PATENT DOCUMENTS 2819879  11/1978  Fed. Rep. of Germany ....... 548/341

Primary Examiner—Alton D. Rollins
Attorney, Agent, or Firm—Sprung, Horn, Kramer & Woods

[57] ABSTRACT

An α-azolyl-keto derivative of the formula

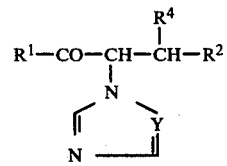

in which
$R^1$ represents optionally substituted alkyl or optionally substituted phenyl,
$R^2$ represents the grouping $-CX^1X^2R^3$ or alkoxycarbonyl,
$R^3$ represents halogen, halogenoalkyl or optionally substituted phenyl,
$R^4$ represents the grouping $-O-CO-R^5$, $-O(S)-R^6$ or $-O-S(O)_n-R^7$, or alkylamino, dialkylamino, optionally substituted phenylamino or halogen,
$R^5$ represents alkyl, halogenoalkyl, alkenyl, alkynyl, cycloalkyl, optionally substituted phenyl, optionally substituted phenylalkyl, alkylamino, dialkylamino or optionally substituted phenylamino,
$R^6$ represents alkyl, alkenyl, alkynyl, cycloalkyl, optionally substituted phenyl or optionally substituted benzyl,
$R^7$ represents alkyl, halogenoalkyl, optionally substituted phenyl or dialkylamino,
n represents 1 or 2,
$X^1$ and $X^2$ each independently represents hydrogen or halogen, and
Y represents a nitrogen atom or the CH group, or a physiologically acceptable acid addition salt or metal salt complex thereof, which possesses fungicidal properties.

9 Claims, No Drawings

COMBATING FUNGI WITH α-AZOLYL-KETO DERIVATIVES

This is a division of application Ser. No. 054,067, filed July 2, 1979 now U.S. Pat. No. 4,316,932, issued Feb. 23, 1982.

The present invention relates to and has for its objects the provision of particular new α-azolyl-keto derivatives which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

The present invention relates to certain new α-azolyl-keto derivatives, to a process for their preparation and to their use as fungicides.

It has already been disclosed that substituted phenoxytriazolyl-keto derivatives and -hydroxy derivatives in general have very good fungicidal properties (see U.S. Pat. No. 3,912,752, issued Oct. 14, 1975 and U.S. Pat. No. 3,952,002, issued Apr. 20, 1976). However, in some fields of use, their action is not always completely satisfactory, especially when low amounts and concentrations are used.

The present invention now provides, as new compounds, the α-azolyl-keto derivatives of the general formula

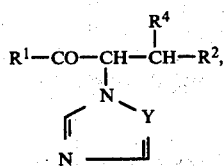

in which
R¹ represents optionally substituted alkyl or optionally substituted phenyl,
R² represents the grouping —CX¹X²R³ or alkoxycarbonyl,
R³ represents halogen, halogenoalkyl or optionally substituted phenyl,
R⁴ represents the grouping —O—CO—R⁵, —O(S)—R⁶ or —O—S(O)ₙ—R⁷, or alkylamino, dialkylamino, optionally substituted phenylamino or halogen,
R⁵ represents alkyl, halogenoalkyl, alkenyl, alkynyl, cycloalkyl, optionally substituted phenyl, optionally substituted phenylalkyl, alkylamino, dialkylamino or optionally substituted phenylamino,
R⁶ represents alkyl, alkenyl, alkynyl, cycloalkyl, optionally substituted phenyl or optionally substituted benzyl,
R⁷ represents alkyl, halogenoalkyl, optionally substituted phenyl or dialkylamino,
n represents the number 1 or 2,
X¹ and X², which may be identical or different, each represent hydrogen or halogen and
Y represents a nitrogen atom or the CH group, and the physiologically acceptable acid-addition salts and metal-salt complexes thereof.

The compounds of the formula (I) have two asymmetric carbon atoms; they can therefore exist in the erythro-form and in the threo-form. In both cases, they exist predominantly as racemates.

Surprisingly, the α-azolyl-keto derivatives according to the invention exhibit a considerably higher fungicidal activity, in particular when used systemically against varied scab and powdery mildew, than substituted phenoxy-triazolyl-keto derivatives and -hydroxy derivatives which are known from the state of the art and are closely related compounds chemically and from the point of view of their action. The substances according to the invention thus represent an enrichment of the art.

Preferably, in formula (I), R¹ represents optionally substituted straight-chain or branched alkyl with 1 to 4 carbon atoms [preferred substituents being halogen (especially fluorine, chlorine and bromine), alkylcarbonyloxy with 1 to 4 carbon atoms in the alkyl part, optionally substituted phenylcarbonyloxy (preferred substituents being halogen, especially fluorine, chlorine and bromine, alkyl with 1 to 2 carbon atoms, halogenoalkyl with 1 to 2 carbon atoms and 1 to 5 halogen atoms, especially fluorine and chlorine, and cyano or nitro), alkyl- or dialkyl-carbamoyloxy with 1 to 4 carbon atoms in each alkyl part, alkylsulphonyloxy with 1 to 4 carbon atoms or optionally substituted phenylsulphonyloxy (preferred substituents on the phenyl part being halogen, especially fluorine, chlorine and bromine, alkyl with 1 to 2 carbon atoms, halogenoalkyl with 1 to 2 carbon atoms and 1 to 5 halogen atoms, especially fluorine and chlorine, and cyano or nitro), dialkylaminosulphonyloxy with 1 to 4 carbon atoms in each alkyl part, alkoxy with 1 to 4 carbon atoms and optionally substituted phenoxy (preferred substituents being halogen, especially fluorine, chlorine and bromine, alkyl with 1 to 2 carbon atoms, halogenoalkyl with 1 to 2 carbon atoms and 1 to 5 halogen atoms, especially fluorine and chlorine, and cyano or nitro)] or phenyl which is optionally mono-substituted or poly-substituted by identical or different substituents chlorine or bromine), cyano, nitro, straight-chain or branched alkyl with up to 4 carbon atoms, cycloalkyl with 5 to 7 carbon atoms (especially cyclohexyl), halogenoalkyl with up to 2 carbon atoms and up to 5 halogen atoms (especially fluorine atoms and chlorine atoms), phenyl, phenoxy or benzyl, the three last radicals being themselves optionally substituted by halogen (especially fluorine or chlorine), cyano or nitro];

R² represents the grouping —CX¹X²R³ or alkoxycarbonyl with 1 to 4 carbon atoms in the alkoxy part;

R³ represents halogen (especially fluorine, chlorine or bromine), halogenoalkyl with 1 to 4 carbon atoms and 1 to 3 halogen atoms (especially fluorine, chlorine or bromine) or optionally substituted phenyl [preferred substituents being halogen (especially fluorine, chlorine or bromine), alkyl with 1 to 2 carbon atoms, halogenoalkyl with 1 to 2 carbon atoms and 1 to 5 halogen atoms (especially fluorine or chlorine), cyano or nitro];

R⁴ represents the grouping —O—CO—R⁵, —O(S)—R⁶ or —O—S(O)ₙ—R⁷, halogen, alkyl- or dialkyl-amino with 1 to 4 carbon atoms in each alkyl part or optionally substituted phenylamino [preferred substituents being halogen, cyano, nitro and alkyl with 1 to 2 carbon atoms];

R⁵ represents straight-chain or branched alkyl with 1 to 8 (especially 1 to 4) carbon atoms, alkenyl or alkynyl with in either case 2 to 4 carbon atoms, halogenoalkyl with 1 to 4 carbon atoms and 1 to 5 halogen atoms (especially fluorine atoms or chlorine atoms), cycloalkyl with 5 to 7 carbon atoms, optionally substituted phenyl or phenylalkyl which is optionally substituted in the phenyl part and has up to 2 carbon atoms in the alkyl part [preferred substituents on the two last-mentioned radicals being halogen, cyano, nitro or alkyl with 1 to 2 carbon atoms], alkylamino or dialkylamino with 1 to 4 carbon atoms in each alkyl part or optionally substituted phenylamino [preferred substituents being halogen, nitro, cyano, alkyl with 1 to 4 carbon atoms, alkoxy and alkylthio with in each case 1 or 2 carbon atoms and halogenoalkyl with up to 2 carbon atoms and up to 5 identical or different halogen atoms (especially fluorine atoms and chlorine atoms)];

$R^6$ represents straight-chain or branched alkyl with 1 to 4 carbon atoms, alkenyl or alkynyl with in either case 2 to 4 carbon atoms, cycloalkyl with 5 to 7 carbon atoms, optionally substituted phenyl or optionally substituted benzyl [preferred substituents on the two last-mentioned radicals being halogen, nitro, cyano, alkyl with 1 to 4 carbon atoms, alkoxy and alkylthio with in each case 1 or 2 carbon atoms and halogenoalkyl with up to 2 carbon atoms and up to 5 identical or different halogen atoms (especially fluorine atoms and chlorine atoms)];

$R^7$ represents alkyl with 1 to 4 carbon atoms, dialkylamino with 1 to 4 carbon atoms, phenyl [which is optionally substituted by chlorine, bromine or methyl] or halogenoalkyl with up to 4 carbon atoms and up to 5 identical or different halogen atoms (especially fluorine atoms and chlorine atoms);

$X^1$ and $X^2$, which may be identical or different, each represent hydrogen, fluorine, chlorine or bromine;

n represents 1 or 2; and

Y represents a nitrogen atom or the CH group.

Particularly preferred compounds of the formula (I) are those in which $R^1$ represents tert.-butyl, sec.-butyl, isopropyl, chloro-tert.-butyl, bromo-tert.-butyl, fluoro-tert.-butyl, 1,3-dichloro-2-methyl-prop-2-yl, 2-methylcarbamoyloxy-prop-2-yl, 2-diethylcarbamoyloxy-prop-2-yl, methylsulphonyloxy-tert.-butyl, phenylsulphonyloxy-tert.-butyl, 4-chlorophenylsulphonyloxy-tert.-butyl, acetoxy-tert.-butyl, ethylcarbonyloxy-tert.-butyl, phenylcarbonyloxy-tert.-butyl, 4-chlorophenylcarbonyloxy-tert.-butyl, diethylaminosulphonyloxy-tert.-butyl, methoxy-tert.-butyl, ethoxy-tert.-butyl, isopropoxy-tert.-butyl, phenoxy-tert.-butyl or 4-chlorophenoxy-tert.-butyl; furthermore, phenyl, chlorophenyl, dichlorophenyl, chloro-methyl-phenyl, bromophenyl, nitrophenyl, biphenylyl, nitrobiphenylyl, chlorobiphenylyl, phenoxyphenyl, chlorophenoxyphenyl, benzylphenyl or chlorobenzylphenyl; $R^2$ represents trichloromethyl, dichlorofluoromethyl, dichloromethyl, chloromethyl, 1,1,2-tribromoethyl, 1,1-dibromoethyl, 1,1-dichloroethyl, 1,1,2-trichloro-prop-1-yl, phenyldichloromethyl, 4-chlorophenyldichloromethyl, methoxycarbonyl or ethoxycarbonyl; $R^4$ represents chlorine, bromine, dimethylamino, ethylmethylamino, diethylamino, dipropylamino, methylamino, ethylamino, propylamino, isopropylamino, phenylamino or chlorophenylamino, or the grouping —O—CO—$R^5$ or —O—(S)—$R^6$; $R^5$ and $R^6$ represent methyl, ethyl, n-propyl, isopropyl, n-butyl, isobutyl, tert.-butyl, sec.-butyl, allyl, propargyl, cyclohexyl or optionally monosubstituted or polysubstituted phenyl or benzyl with chlorine, bromine or methyl as substituents; $R^5$ alternatively represents chloromethyl, dichloromethyl, methyl or ethyl-amino, dimethyl- or diethyl-amino, phenylamino or chlorophenylamino; $R^7$ represents methyl, ethyl, n-propyl, isopropyl, tert.-butyl, chloromethyl, dichloromethyl, trichloromethyl, fluoromethyl, trifluoromethyl, phenyl, chlorophenyl, dimethyl or diethylamino; n represents 1 or 2; and Y represents a nitrogen atom or the CH group.

Specific compounds of the general formula (I) which may be mentioned, in addition to the compounds mentioned in the preparative examples given later in this specification, are:

TABLE 1

$$R^1—CO—CH—CH—R^2 \atop \underset{N}{|} \atop \underset{\phantom{N}}{N\diagdown_Y}$$
(I)
with $R^4$ on the second CH

| $R^1$ | $R^2$ | $R^4$ | Y |
| --- | --- | --- | --- |
| C(CH₃)₃ | —CCl₂—CHCl—CH₃ | —O—CO—CH₃ | N(CH) |
| C(CH₃)₃ | —CO—O—C₂H₅ | —O—CO—CH₃ | N(CH) |
| C(CH₃)₃ | —CCl₂—CHCl—CH₃ | —O—CO—C₂H₅ | N(CH) |
| C(CH₃)₃ | —CO—O—C₂H₅ | —O—CO—C₂H₅ | N(CH) |
|  | —CCl₃ | —O—CO—CH₃ | N(CH) |
|  | —CO—O—C₂H₅ | —O—CO—CH₃ | N(CH) |
|  | —CCl₂—CHCl—CH₃ | —O—CO—CH₃ | N(CH) |
| 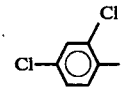 | —CCl₃ | —O—CO—CH₃ | N(CH) |

COMBATING FUNGI WITH α-AZOLYL-KETO DERIVATIVES

This is a division of application Ser. No. 054,067, filed July 2, 1979 now U.S. Pat. No. 4,316,932, issued Feb. 23, 1982.

The present invention relates to and has for its objects the provision of particular new α-azolyl-keto derivatives which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

The present invention relates to certain new α-azolyl-keto derivatives, to a process for their preparation and to their use as fungicides.

It has already been disclosed that substituted phenoxytriazolyl-keto derivatives and -hydroxy derivatives in general have very good fungicidal properties (see U.S. Pat. No. 3,912,752, issued Oct. 14, 1975 and U.S. Pat. No. 3,952,002, issued Apr. 20, 1976). However, in some fields of use, their action is not always completely satisfactory, especially when low amounts and concentrations are used.

The present invention now provides, as new compounds, the α-azolyl-keto derivatives of the general formula

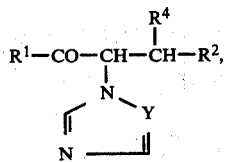

in which
R¹ represents optionally substituted alkyl or optionally substituted phenyl,
R² represents the grouping —CX¹X²R³ or alkoxycarbonyl,
R³ represents halogen, halogenoalkyl or optionally substituted phenyl,
R⁴ represents the grouping —O—CO—R⁵, —O(S)—R⁶ or —O—S(O)ₙ—R⁷, or alkylamino, dialkylamino, optionally substituted phenylamino or halogen,
R⁵ represents alkyl, halogenoalkyl, alkenyl, alkynyl, cycloalkyl, optionally substituted phenyl, optionally substituted phenylalkyl, alkylamino, dialkylamino or optionally substituted phenylamino,
R⁶ represents alkyl, alkenyl, alkynyl, cycloalkyl, optionally substituted phenyl or optionally substituted benzyl,
R⁷ represents alkyl, halogenoalkyl, optionally substituted phenyl or dialkylamino,
n represents the number 1 or 2,
X¹ and X², which may be identical or different, each represent hydrogen or halogen and
Y represents a nitrogen atom or the CH group, and the physiologically acceptable acid-addition salts and metal-salt complexes thereof.

The compounds of the formula (I) have two asymmetric carbon atoms; they can therefore exist in the erythro-form and in the threo-form. In both cases, they exist predominantly as racemates.

Surprisingly, the α-azolyl-keto derivatives according to the invention exhibit a considerably higher fungicidal activity, in particular when used systemically against varied scab and powdery mildew, than substituted phenoxy-triazolyl-keto derivatives and -hydroxy derivatives which are known from the state of the art and are closely related compounds chemically and from the point of view of their action. The substances according to the invention thus represent an enrichment of the art.

Preferably, in formula (I), R¹ represents optionally substituted straight-chain or branched alkyl with 1 to 4 carbon atoms [preferred substituents being halogen (especially fluorine, chlorine and bromine), alkylcarbonyloxy with 1 to 4 carbon atoms in the alkyl part, optionally substituted phenylcarbonyloxy (preferred substituents being halogen, especially fluorine, chlorine and bromine, alkyl with 1 to 2 carbon atoms, halogenoalkyl with 1 to 2 carbon atoms and 1 to 5 halogen atoms, especially fluorine and chlorine, and cyano or nitro), alkyl- or dialkyl-carbamoyloxy with 1 to 4 carbon atoms in each alkyl part, alkylsulphonyloxy with 1 to 4 carbon atoms or optionally substituted phenylsulphonyloxy (preferred substituents on the phenyl part being halogen, especially fluorine, chlorine and bromine, alkyl with 1 to 2 carbon atoms, halogenoalkyl with 1 to 2 carbon atoms and 1 to 5 halogen atoms, especially fluorine and chlorine, and cyano or nitro), dialkylaminosulphonyloxy with 1 to 4 carbon atoms in each alkyl part, alkoxy with 1 to 4 carbon atoms and optionally substituted phenoxy (preferred substituents being halogen, especially fluorine, chlorine and bromine, alkyl with 1 to 2 carbon atoms, halogenoalkyl with 1 to 2 carbon atoms and 1 to 5 halogen atoms, especially fluorine and chlorine, and cyano or nitro)] or phenyl which is optionally mono-substituted or poly-substituted by identical or different substituents chlorine or bromine), cyano, nitro, straight-chain or branched alkyl with up to 4 carbon atoms, cycloalkyl with 5 to 7 carbon atoms (especially cyclohexyl), halogenoalkyl with up to 2 carbon atoms and up to 5 halogen atoms (especially fluorine atoms and chlorine atoms), phenyl, phenoxy or benzyl, the three last radicals being themselves optionally substituted by halogen (especially fluorine or chlorine), cyano or nitro];

R² represents the grouping —CX¹X²R³ or alkoxycarbonyl with 1 to 4 carbon atoms in the alkoxy part;

R³ represents halogen (especially fluorine, chlorine or bromine), halogenoalkyl with 1 to 4 carbon atoms and 1 to 3 halogen atoms (especially fluorine, chlorine or bromine) or optionally substituted phenyl [preferred substituents being halogen (especially fluorine, chlorine or bromine), alkyl with 1 to 2 carbon atoms, halogenoalkyl with 1 to 2 carbon atoms and 1 to 5 halogen atoms (especially fluorine or chlorine), cyano or nitro];

R⁴ represents the grouping —O—CO—R⁵, —O(S)—R⁶ or —O—S(O)ₙ—R⁷, halogen, alkyl- or dialkylamino with 1 to 4 carbon atoms in each alkyl part or optionally substituted phenylamino [preferred substituents being halogen, cyano, nitro and alkyl with 1 to 2 carbon atoms];

R⁵ represents straight-chain or branched alkyl with 1 to 8 (especially 1 to 4) carbon atoms, alkenyl or alkynyl with in either case 2 to 4 carbon atoms, halogenoalkyl with 1 to 4 carbon atoms and 1 to 5 halogen atoms (especially fluorine atoms or chlorine atoms), cycloalkyl with 5 to 7 carbon atoms, optionally substituted phenyl or phenylalkyl which is optionally substituted in the phenyl part and has up to 2 carbon atoms in the alkyl part [preferred substituents on the two last-mentioned radicals being halogen, cyano, nitro or alkyl with 1 to 2 carbon atoms], alkylamino or dialkylamino with 1 to 4 carbon atoms in each alkyl part or optionally substituted phenylamino [preferred substituents being halogen, nitro, cyano, alkyl with 1 to 4 carbon atoms, alkoxy and alkylthio with in each case 1 or 2 carbon atoms and halogenoalkyl with up to 2 carbon atoms and up to 5 identical or different halogen atoms (especially fluorine atoms and chlorine atoms)];

$R^6$ represents straight-chain or branched alkyl with 1 to 4 carbon atoms, alkenyl or alkynyl with in either case 2 to 4 carbon atoms, cycloalkyl with 5 to 7 carbon atoms, optionally substituted phenyl or optionally substituted benzyl [preferred substituents on the two last-mentioned radicals being halogen, nitro, cyano, alkyl with 1 to 4 carbon atoms, alkoxy and alkylthio with in each case 1 or 2 carbon atoms and halogenoalkyl with up to 2 carbon atoms and up to 5 identical or different halogen atoms (especially fluorine atoms and chlorine atoms)];

$R^7$ represents alkyl with 1 to 4 carbon atoms, dialkylamino with 1 to 4 carbon atoms, phenyl [which is optionally substituted by chlorine, bromine or methyl] or halogenoalkyl with up to 4 carbon atoms and up to 5 identical or different halogen atoms (especially fluorine atoms and chlorine atoms);

$X^1$ and $X^2$, which may be identical or different, each represent hydrogen, fluorine, chlorine or bromine;

n represents 1 or 2; and

Y represents a nitrogen atom or the CH group.

Particularly preferred compounds of the formula (I) are those in which $R^1$ represents tert.-butyl, sec.-butyl, isopropyl, chloro-tert.-butyl, bromo-tert.-butyl, fluoro-tert.-butyl, 1,3-dichloro-2-methyl-prop-2-yl, 2-methylcarbamoyloxy-prop-2-yl, 2-diethylcarbamoyloxy-prop-2-yl, methylsulphonyloxy-tert.-butyl, phenylsulphonyloxy-tert.-butyl, 4-chlorophenylsulphonyloxy-tert.-butyl, acetoxy-tert.-butyl, ethylcarbonyloxy-tert.-butyl, phenylcarbonyloxy-tert.-butyl, 4-chlorophenylcarbonyloxy-tert.-butyl, diethylaminosulphonyloxy-tert.-butyl, methoxy-tert.-butyl, ethoxy-tert.-butyl, isopropoxy-tert.-butyl, phenoxy-tert.-butyl or 4-chlorophenoxy-tert.-butyl; furthermore, phenyl, chlorophenyl, dichlorophenyl, chloro-methyl-phenyl, bromophenyl, nitrophenyl, biphenylyl, nitrobiphenylyl, chlorobiphenylyl, phenoxyphenyl, chlorophenoxyphenyl, benzylphenyl or chlorobenzylphenyl; $R^2$ represents trichloromethyl, dichlorofluoromethyl, dichloromethyl, chloromethyl, 1,1,2-tribromoethyl, 1,1-dibromoethyl, 1,1-dichloroethyl, 1,1,2-trichloro-prop-1-yl, phenyldichloromethyl, 4-chlorophenyldichloromethyl, methoxycarbonyl or ethoxycarbonyl; $R^4$ represents chlorine, bromine, dimethylamino, ethylmethylamino, diethylamino, dipropylamino, methylamino, ethylamino, propylamino, isopropylamino, phenylamino or chlorophenylamino, or the grouping —O—CO—$R^5$ or —O—(S)—$R^6$; $R^5$ and $R^6$ represent methyl, ethyl, n-propyl, isopropyl, n-butyl, isobutyl, tert.-butyl, sec.-butyl, allyl, propargyl, cyclohexyl or optionally monosubstituted or polysubstituted phenyl or benzyl with chlorine, bromine or methyl as substituents; $R^5$ alternatively represents chloromethyl, dichloromethyl, methyl or ethyl-amino, dimethyl- or diethyl-amino, phenylamino or chlorophenylamino; $R^7$ represents methyl, ethyl, n-propyl, isopropyl, tert.-butyl, chloromethyl, dichloromethyl, trichloromethyl, fluoromethyl, trifluoromethyl, phenyl, chlorophenyl, dimethyl or diethylamino; n represents 1 or 2; and Y represents a nitrogen atom or the CH group.

Specific compounds of the general formula (I) which may be mentioned, in addition to the compounds mentioned in the preparative examples given later in this specification, are:

TABLE 1

| $R^1$ | $R^2$ | $R^4$ | Y |
|---|---|---|---|
| C(CH₃)₃ | —CCl₂—CHCl—CH₃ | —O—CO—CH₃ | N(CH) |
| C(CH₃)₃ | —CO—O—C₂H₅ | —O—CO—CH₃ | N(CH) |
| C(CH₃)₃ | —CCl₂—CHCl—CH₃ | —O—CO—C₂H₅ | N(CH) |
| C(CH₃)₃ | —CO—O—C₂H₅ | —O—CO—C₂H₅ | N(CH) |
|  | —CCl₃ | —O—CO—CH₃ | N(CH) |
|  | —CO—O—C₂H₅ | —O—CO—CH₃ | N(CH) |
|  | —CCl₂—CHCl—CH₃ | —O—CO—CH₃ | N(CH) |
| 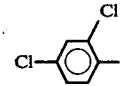 | —CCl₃ | —O—CO—CH₃ | N(CH) |

TABLE 1-continued $$R^1-CO-CH(N)-CH(R^4)-R^2 \quad \text{(I)}$$

(with N-Y-N=CH ring)

| R¹ | R² | R⁴ | Y |
|---|---|---|---|
| 2,4-dichlorophenyl (CH₃ substituted) | −CCl₂−CHCl−CH₃ | −O−CO−CH₃ | N(CH) |
| 4-chlorophenyl | −CCl₃ | −O−CO−CH₃ | N(CH) |
| 4-chlorophenyl | −CCl₂−CHCl−CH₃ | −O−CO−CH₃ | N(CH) |
| biphenyl-4-yl | −CCl₃ | −O−CO−CH₃ | N(CH) |
| biphenyl-4-yl | −CCl₂−CHCl−CH₃ | −O−CO−CH₃ | N(CH) |
| 4'-chlorobiphenyl-4-yl | −CCl₃ | −O−CO−CH₃ | N(CH) |
| 4'-chlorobiphenyl-4-yl | −CCl₂−CHCl−CH₃ | −O−CO−CH₃ | N(CH) |
| ClCH₂−C(CH₃)₂− | −CCl₃ | −O−CO−CH₃ | N(CH) |
| ClCH₂−C(CH₃)₂− | −CCl₂−CHCl−CH₃ | −O−CO−CH₃ | N(CH) |
| CH₃−CO−O−CH₂−C(CH₃)₂− | −CCl₃ | −O−CO−CH₃ | N(CH) |
| CH₃−CO−O−CH₂−C(CH₃)₂− | −CCl₂−CHCl−CH₃ | −O−CH−CH₃ | N(CH) |
| CH₃(H)N−CO−O−C(CH₃)₂− | −CCl₃ | −O−CO−CH₃ | N(CH) |
| CH₃(H)N−CO−O−C(CH₃)₂− | −CCl₂−CHCl−CH₃ | −O−CO−CH₃ | N(CH) |
| 4-chloro-2-methylphenyl | −CCl₃ | −O−CO−CH₃ | N(CH) |
| 4-chloro-2-methylphenyl | −CCl₂−CHCl−CH₃ | −O−CO−CH₃ | N(CH) |
| 4-phenoxyphenyl | −CCl₃ | −O−CO−CH₃ | N(CH) |

TABLE 1-continued $$R^1-CO-CH(N)-CH(R^4)-R^2$$
(I)

with ring containing N, Y, =N, =CH

| R¹ | R² | R⁴ | Y |
|---|---|---|---|
| C₆H₅—O—C₆H₄— | —CCl₂—CHCl—CH₃ | —O—CO—CH₃ | N(CH) |
| Cl—C₆H₄—O—C₆H₄— | —CCl₃ | —O—CO—CH₃ | N(CH) |
| Br—C₆H₄— | —CCl₃ | —O—CO—CH₃ | N(CH) |
| Br—C₆H₄— | —CCl₂—CHCl—CH₃ | —O—CO—CH₃ | N(CH) |
| CH₃—SO₂—O—CH₂—C(CH₃)₂— | —CCl₃ | —O—CO—CH₃ | N(CH) |
| CH₃—SO₂—O—CH₂—C(CH₃)₂— | —CCl₂—CHCl—CH₃ | —O—CO—CH₃ | N(CH) |
| BrCH₂—C(CH₃)₂— | —CCl₃ | —O—CC—CH₃ | N(CH) |
| BrCH₂—C(CH₃)₂— | —CCl₂—CHCl—CH₃ | —O—CO—CH₃ | N(CH) |
| C(CH₃)₃ | —CCl₂—CHCl—CH₃ | —O—CO—NHCH₃ | N(CH) |
| C(CH₃)₃ | —CO—O—C₂H₅ | —O—CO—NHCH₃ | N(CH) |
| Cl—C₆H₄— | —CCl₃ | —O—CO—NHCH₃ | N(CH) |
| Cl—C₆H₄— | —CCl₂—CHCl—CH₃ | —O—CO—NHCH₃ | N(CH) |
| Cl,Cl—C₆H₃— | —CCl₃ | —O—CO—NHCH₃ | N(CH) |
| Cl,Cl—C₆H₃— | —CCl₂—CHCl—CH₃ | —O—CO—NHCH₃ | N(CH) |
| C₆H₅—C₆H₄— | —CCl₃ | —O—CO—NHCH₃ | N(CH) |
| C₆H₅—C₆H₄— | —CCl₂—CHCl—CH₃ | —O—CO—NHCH₃ | N(CH) |
| Cl—C₆H₄—C₆H₄— | —CCl₃ | —O—CO—NHCH₃ | N(CH) |
| Cl—C₆H₄—C₆H₄— | —CCl₂—CHCl—CH₃ | —O—CO—NHCH₃ | N(CH) |
| C₆H₅—O—C₆H₄— | —CCl₃ | —O—CO—NHCH₃ | N(CH) |
| C₆H₅—O—C₆H₄— | —CHCl₂—CHCl—CH₃ | —O—CO—NHCH₃ | N(CH) |

TABLE 1-continued $$R^1-CO-CH(-\underset{\underset{N=}{N-Y}}{N})-CH(R^4)-R^2 \quad (I)$$

| R¹ | R² | R⁴ | Y |
|---|---|---|---|
| Cl—C₆H₄—O—C₆H₄— | —CCl₃ | —O—CO—NHCH₃ | N(CH) |
| Cl—C₆H₄—O—C₆H₄— | —CCl₂—CHCl—CH₃ | —O—CO—NHCH₃ | N(CH) |
| ClCH₂—C(CH₃)₂— | —CCl₃ | —O—CO—NHCH₃ | N(CH) |
| ClCH₂—C(CH₃)₂— | —CCl₂—CHCl—CH₃ | —O—CO—NHCH₃ | N(CH) |
| CH₃—COO—CH₂—C(CH₃)₂— | —CCl₃ | —O—CO—NHCH₃ | N(CH) |
| CH₃—COO—CH₂—C(CH₃)₂— | —CCl₂—CHCl—CH₃ | —O—CO—NHCH₃ | N(CH) |
| CH₃—SO₂—CH₂—C(CH₃)₂— | —CCl₃ | —O—CO—NHCH₃ | N(CH) |
| CH₃—SO₂—CH₂—C(CH₃)₂— | —CCl₂—CHCl—CH₃ | —O—CO—NHCH₃ | N(CH) |
| CH₃NH—COO—CH₂—C(CH₃)₂— | —CCl₃ | —O—CO—NHCH₃ | N(CH) |
| CH₃NH—COO—CH₂—C(CH₃)₂— | —CCl₂—CHCl—CH₃ | —O—CO—NHCH₃ | N(CH) |
| CH₃O—C(CH₃)₂— | —CCl₃ | —O—CO—NHCH₃ | N(CH) |
| CH₃O—C(CH₃)₂— | —CCl₂—CHCl—CH₃ | —O—CO—NHCH₃ | N(CH) |
| C(CH₃)₃ | —CCl₂—CHCl—CH₃ | Cl | N(CH) |
| C(CH₃)₃ | —CO—O—C₂H₅ | Cl | N(CH) |
| Cl—C₆H₄— | —CCl₃ | Cl | N(CH) |
| Cl—C₆H₄— | —CCl₂—CHCl—CH₃ | Cl | N(CH) |
| ClCH₂—C(CH₃)₂— | —CCl₃ | Cl | N(CH) |
| ClCH₂—C(CH₃)₂— | —CCl₂—CHCl—CH₃ | Cl | N(CH) |
| 3,4-Cl₂-C₆H₃— | —CCl₃ | Cl | N(CH) |
| 3,4-Cl₂-C₆H₃— | CCl₂—CHCl—CH₃ | Cl | N(CH) |
| C₆H₅—C₆H₄— | —CCl₃ | Cl | N(CH) |
| C₆H₅—C₆H₄— | —CCl₂—CHCl—CH₃ | Cl | N(CH) |
| Cl—C₆H₄—C₆H₄— | —CCl₃ | Cl | N(CH) |
| Cl—C₆H₄—C₆H₄— | —CCl₂—CHCl—CH₃ | Cl | N(CH) |
| C₆H₅—O—C₆H₄— | —CCl₃ | Cl | N(CH) |
| C₆H₅—O—C₆H₄— | —CCl₂—CHCl—CH₃ | Cl | N(CH) |
| Cl—C₆H₄—O—C₆H₄— | —CCl₃ | Cl | N(CH) |

TABLE 1-continued $$R^1-CO-\underset{\underset{N=\!\!\!=\!\!\!\diagup}{\overset{|}{N}}\diagdown_{Y}}{\overset{R^4}{\overset{|}{CH}}}-CH-R^2 \quad (I)$$

| R¹ | R² | R⁴ | Y |
|---|---|---|---|
| 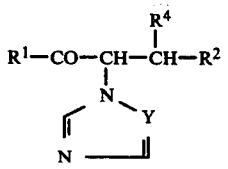 | —CCl₂—CHCl—CH₃ | Cl | N(CH) |
| CH₃—COO—CH₂—C(CH₃)₂— | —CCl₃ | Cl | N(CH) |
| CH₃—COO—CH₂—C(CH₃)₂— | —CCl₂—CHCl—CH₃ | Cl | N(CH) |
| CH₃—SO₂—CH₂—C(CH₃)₂— | —CCl₃ | Cl | N(CH) |
| CH₃—SO₂—CH₂—C(CH₃)₂— | —CCl₂—CHCl—CH₃ | Cl | N(CH) |
| CH₃NH—COO—CH₂—C(CH₃)₂— | —CCl₃ | Cl | N(CH) |
| CH₃NH—COO—CH₂—C(CH₃)₂— | —CCl₂—CHCl—CH₃ | Cl | N(CH) |
| CH₃O—C(CH₃)₂— | —CCl₃ | Cl | N(CH) |
| CH₃O—C(CH₃)₂— | —CCl₂—CHCl—CH₃ | Cl | N(CH) |
| C(CH₃)₃ | —CCl₂—CHCl—CH₃ | —OCH₃ | N(CH) |
| C(CH₃)₃ | —CO—O—C₂H₅ | —OCH₃ | N(CH) |
| 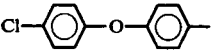 | —CCl₃ | —OCH₃ | N(CH) |
|  | —CCl₂—CHCl—CH₃ | —OCH₃ | N(CH) |
|  | —CO—O—C₂H₅ | —OCH₃ | N(CH) |
|  | —CCl₃ | —OCH₃ | N(CH) |
|  | —CCl₂—CHCl—CH₃ | —OCH₃ | N(CH) |
|  | —CCl₃ | —OCH₃ | N(CH) |
|  | —CCl₂—CHCl—CH₃ | —OCH₃ | N(CH) |
|  | —CCl₃ | —OCH₃ | N(CH) |
|  | —CCl₂—CHCl—CH₃ | —OCH₃ | N(CH) |
|  | —CCl₃ | —OCH₃ | N(CH) |
|  | —CCl₂—CHCl—CH₃ | —OCH₃ | N(CH) |
|  | —CCl₃ | —OCH₃ | N(CH) |
|  | —CCl₂—CHCl—CH₃ | —OCH₃ | N(CH) |

TABLE 1-continued

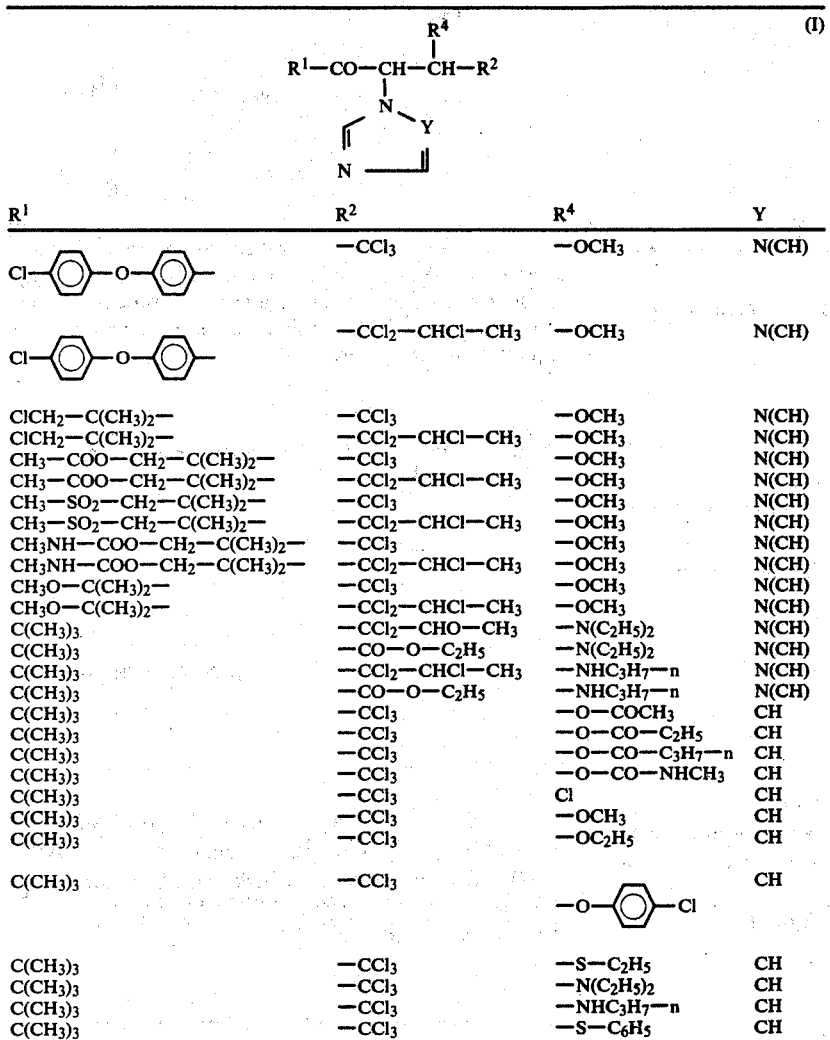

| R¹ | R² | R⁴ | Y |
|---|---|---|---|
| Cl—⟨phenyl⟩—O—⟨phenyl⟩— | —CCl₃ | —OCH₃ | N(CH) |
| Cl—⟨phenyl⟩—O—⟨phenyl⟩— | —CCl₂—CHCl—CH₃ | —OCH₃ | N(CH) |
| ClCH₂—C(CH₃)₂— | —CCl₃ | —OCH₃ | N(CH) |
| ClCH₂—C(CH₃)₂— | —CCl₂—CHCl—CH₃ | —OCH₃ | N(CH) |
| CH₃—COO—CH₂—C(CH₃)₂— | —CCl₃ | —OCH₃ | N(CH) |
| CH₃—COO—CH₂—C(CH₃)₂— | —CCl₂—CHCl—CH₃ | —OCH₃ | N(CH) |
| CH₃—SO₂—CH₂—C(CH₃)₂— | —CCl₃ | —OCH₃ | N(CH) |
| CH₃—SO₂—CH₂—C(CH₃)₂— | —CCl₂—CHCl—CH₃ | —OCH₃ | N(CH) |
| CH₃NH—COO—CH₂—C(CH₃)₂— | —CCl₃ | —OCH₃ | N(CH) |
| CH₃NH—COO—CH₂—C(CH₃)₂— | —CCl₂—CHCl—CH₃ | —OCH₃ | N(CH) |
| CH₃O—C(CH₃)₂— | —CCl₃ | —OCH₃ | N(CH) |
| CH₃O—C(CH₃)₂— | —CCl₂—CHCl—CH₃ | —OCH₃ | N(CH) |
| C(CH₃)₃ | —CCl₂—CHO—CH₃ | —N(C₂H₅)₂ | N(CH) |
| C(CH₃)₃ | —CO—O—C₂H₅ | —N(C₂H₅)₂ | N(CH) |
| C(CH₃)₃ | —CCl₂—CHCl—CH₃ | —NHC₃H₇—n | N(CH) |
| C(CH₃)₃ | —CO—O—C₂H₅ | —NHC₃H₇—n | N(CH) |
| C(CH₃)₃ | —CCl₃ | —O—COCH₃ | CH |
| C(CH₃)₃ | —CCl₃ | —O—CO—C₂H₅ | CH |
| C(CH₃)₃ | —CCl₃ | —O—CO—C₃H₇—n | CH |
| C(CH₃)₃ | —CCl₃ | —O—CO—NHCH₃ | CH |
| C(CH₃)₃ | —CCl₃ | Cl | CH |
| C(CH₃)₃ | —CCl₃ | —OCH₃ | CH |
| C(CH₃)₃ | —CCl₃ | —OC₂H₅ | CH |
| C(CH₃)₃ | —CCl₃ | —O—⟨phenyl⟩—Cl | CH |
| C(CH₃)₃ | —CCl₃ | —S—C₂H₅ | CH |
| C(CH₃)₃ | —CCl₃ | —N(C₂H₅)₂ | CH |
| C(CH₃)₃ | —CCl₃ | —NHC₃H₇—n | CH |
| C(CH₃)₃ | —CCl₃ | —S—C₆H₅ | CH |

The invention also provides a process for the preparation of an α-azolyl-keto derivative of the formula (I), in which an α-azolyl-β-hydroxy-ketone of the general formula

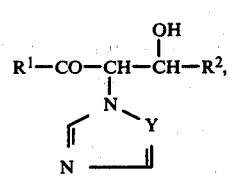  (II)

in which

R¹, R² and Y have the meanings stated above, (a) is reacted with an acid halide of the general formula

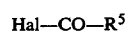 (III), in which

R⁵ has the meaning stated above and

Hal represents halogen, especially chlorine or bromine, if appropriate in the presence of a solvent and if appropriate in the presence of an acid-binding agent, or (b) is reacted with an acid anhydride of the general formula

R⁵—CO—O—CO—R⁵   (IV), in which

R⁵ has the meaning stated above, in the presence of a solvent and if appropriate in the presence of a catalyst, or (c) is reacted with an isocyanate of the general formula

   (V), in which

R⁸ represents alkyl or optionally substituted phenyl, in the presence of a solvent and if appropriate in the presence of a catalyst, or (d) is reacted with a halogenating agent, if appropriate in the presence of a solvent, or in which an α-azolyl-β-halogeno-ketone, which can be obtained by process variant (d), of the general formula

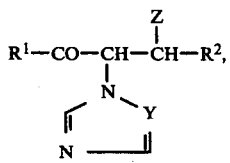 (Ia)

in which
R[1], R[2] and Y have the meanings stated above and
Z represents halogen,
(e) is reacted with a (thio)alcohol of the general formula

 (VI), in which
R[6] has the meaning stated above and
M represents an alkali metal or ammonium, if appropriate in the presence of a solvent, or
(f) is reacted with an amine of the general formula

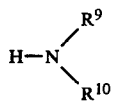 (VII)

in which
R[9] represents hydrogen or alkyl and
R[10] represents alkyl or optionally substituted phenyl, in the presence of a solvent and in the presence of an acid-binding agent, or
(g) is reacted with a salt of the formula

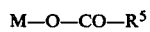 (VIII)

or

 (IX), in which
R[5], R[7], M and n have the meanings stated above, in the presence of a solvent.

Furthermore, the α-azolyl-keto derivatives of the formula (I) obtainable according to the invention can be converted into the salts by reaction with acids, or the corresponding metal salt complexes can be obtained by reaction with metal salts.

If, for example, 1,1,1-trichloro-2-hydroxy-3-(1,2,4-triazol-1-yl)-5,5-dimethyl-hexan-4-one and dichloroacetyl chloride are used as starting materials in process variant (a), the course of the reaction can be represented by the equation which follows:

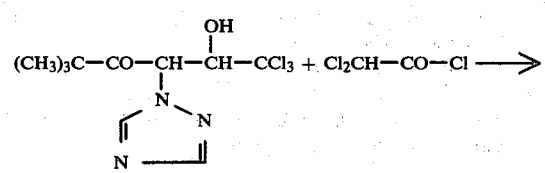

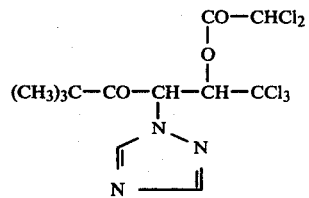

If, for example, 1,1,1-trichloro-2-hydroxy-3-(1,2,4-triazol-1-yl)-5,5-dimethyl-hexan-4-one and acetic anhydride are used as starting materials in process variant (b), the course of the reaction can be represented by the equation which follows:

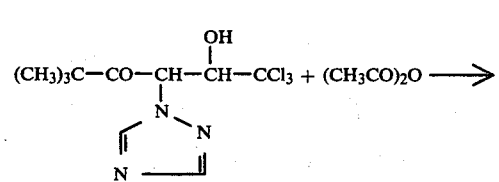

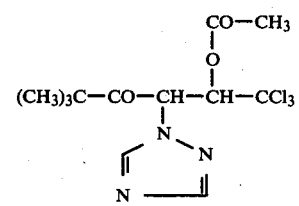

If, for example, 1,1,1-trichloro-2-hydroxy-3-(imidazol-1-yl)-5,5-dimethyl-hexan-4-one and methyl isocyanate are used as starting materials in process variant (c), the course of the reaction can be represented by the equation which follows:

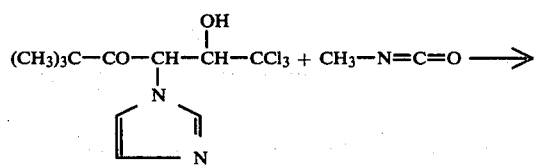

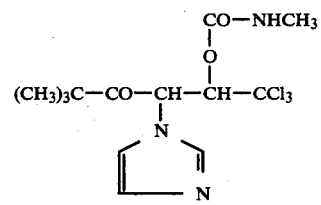

If, for example, 2,4-dichlorophenyl 3,3,4-trichloro-2-hydroxy-1-(1,2,4-triazol-1-yl)-pentyl ketone and thionyl chloride are used as starting materials in process variant (d), the course of the reaction can be represented by the equation which follows:

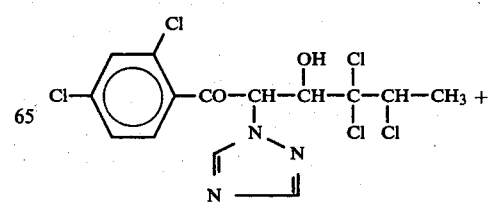

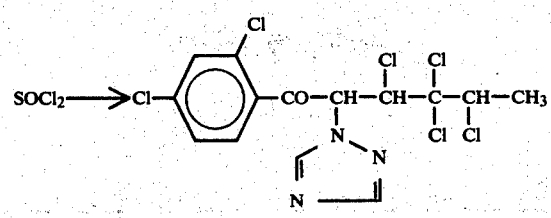

If, for example, 1,1,1,2-tetrachloro-3-(1,2,4-triazol-1-yl)-5,5-dimethyl-hexan-4-one and sodium methylate are used as starting materials in process variant (e), the course of the reaction can be represented by the equation which follows:

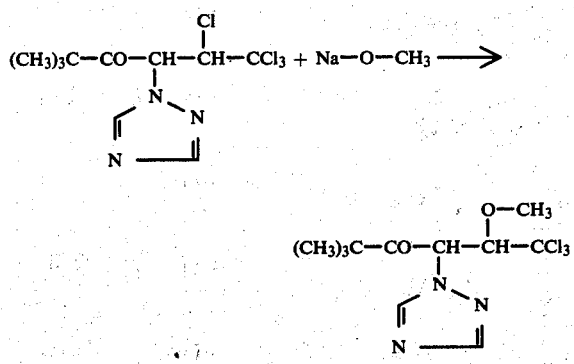

If, for example, 1,1,1,2-tetrachloro-3-(1,2,4-triazol-1-yl)-5,5-dimethyl-hexan-4-one and diethylamine are used as starting materials in process variant (f), the course of the reaction can be represented by the equation which follows:

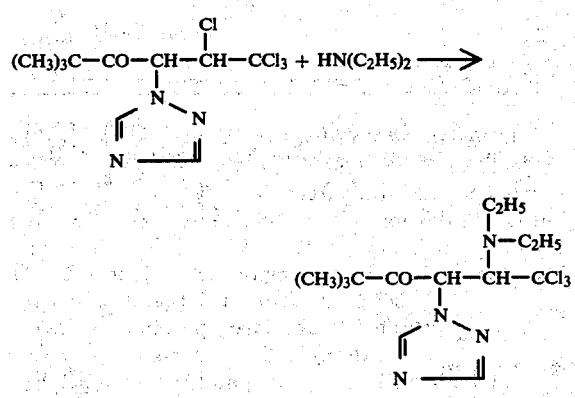

If, for example, 1,1,1,2-tetrachloro-3-(1,2,4-triazol-1-yl)-5,5-dimethyl-hexan-4-one and sodium acetate are used as starting materials in process variant (g), the course of the reaction can be represented by the equation which follows:

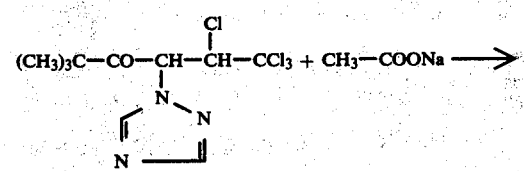

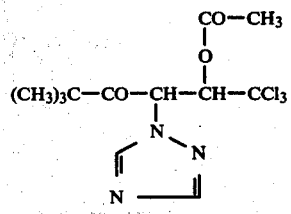

The formula (II) provides a general definition of the α-azolyl-β-hydroxy-ketones to be used as starting substances for process variants (a), (b), (c) and (d) according to the invention. In this formula, $R^1$, $R^2$ and Y preferably represent those radicals which have already been mentioned as preferred in the case of the compounds of the formula (I).

The α-azolyl-β-hydroxy-ketones of the formula (II) and their preparation are described in application Ser. No. 54,061, filed July 2, 1979, (corresponding to German Patent Application No. P2832233.0, filed on July 21, 1978), now U.S. Pat. No. 4,291,047, the disclosure of which is incorporated herein by reference.

They are obtained by reacting α-azolyl-ketones of the general formula

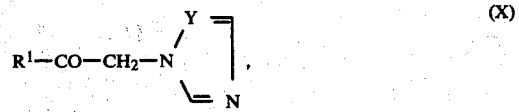

in which $R^1$ and Y have the meanings stated above, with aldehydes of the general formula

in which $R^2$ has the meaning stated above, in the presence of an inert organic solvent, for example methylene chloride and, in particular, glacial acetic acid, and in the presence of a catalyst, for example titanium tetrachloride and, in particular, sodium acetate, at temperatures between 20° and 100° C. (see also the preparative examples).

α-Azolyl-ketones of the formula (X) are known (see DE-OS (German Published Specification) No. 2,063,857 and pending U.S. patent application Ser. No. 792,756, filed May 2, 1977 and can be obtained by the processes described therein, for example by reacting corresponding α-halogeno-ketones with 1,2,4-triazole or imidazole in the presence of an inert organic solvent, for example acetone, and in the presence of an acid-binding agent, for example sodium carbonate, preferably at the boil (see also the preparative examples).

Examples which may be mentioned of the starting materials of the formula (II) (Y represents N or CH and the 1,2,4-triazol-1-yl radical or imidazol-1-yl radical is thus present) are:

TABLE 2

$$R^1-CO-CH(-N(=CH-N=)Y)-CH(OH)-R^2$$

| $R^1$ | $R^2$ |
|---|---|
| $C(CH_3)_3$ | $-CCl_3$ |
| $C(CH_3)_3$ | $-CCl_2-CHCl-CH_3$ |
| $C(CH_3)_3$ | $-CO-OC_2H_5$ |
| $ClCH_2-C(CH_3)_2-$ | $-CCl_3$ |
| $ClCH_2-C(CH_3)_2-$ | $-CCl_2-CHCl-CH_3$ |
| $BrCH_2-C(CH_3)_2-$ | $-CCl_3$ |
| $BrCH_2-C(CH_3)_2-$ | $-CCl_2-CHCl-CH_3$ |
| $CH_3-COO-CH_2-C(CH_3)_2-$ | $-CCl_3$ |
| $CH_3-COO-CH_2-C(CH_3)_2-$ | $-CCl_2-CHCl-CH_3$ |
| $CH_3-SO_2-CH_2-C(CH_3)_2-$ | $-CCl_3$ |
| $CH_3-SO_2-CH_2-C(CH_3)_2-$ | $-CCl_2-CHCl-CH_3$ |
| $CH_3NH-COO-CH_2-C(CH_3)_2-$ | $-CCl_3$ |
| $CH_3NH-COO-CH_2-C(CH_3)_2-$ | $-CCl_2-CHCl-CH_3$ |
| 4-Br-C$_6$H$_4-$ | $-CCl_3$ |
| 4-Br-C$_6$H$_4-$ | $-CCl_2-CHCl-CH_3$ |
| C$_6$H$_5-$ | $-CCl_3$ |
| C$_6$H$_5-$ | $-CCl_2-CHCl-CH_3$ |
| C$_6$H$_5-$ | $-CO-OC_2H_5$ |
| 4-Cl-C$_6$H$_4-$ | $-CCl_3$ |
| 4-Cl-C$_6$H$_4-$ | $-CCl_2-CHCl-CH_3$ |
| 3,4-Cl$_2$-C$_6$H$_3-$ | $-CCl_3$ |
| 3,4-Cl$_2$-C$_6$H$_3-$ | $-CCl_2-CHCl-CH_3$ |
| 4-Cl-3-CH$_3$-C$_6$H$_3-$ | $-CCl_3$ |
| 4-Cl-3-CH$_3$-C$_6$H$_3-$ | $-CCl_2-CHCl-CH_3$ |
| 3,4-Cl$_2$-C$_6$H$_3-$ (alt) | $-CCl_3$ |
| 3,4-Cl$_2$-C$_6$H$_3-$ (alt) | $-CCl_2-CHCl-CH_3$ |
| 4-C$_6$H$_5$-C$_6$H$_4-$ | $-CCl_3$ |
| 4-C$_6$H$_5$-C$_6$H$_4-$ | $-CCl_2-CHCl-CH_3$ |
| 4-(4-Cl-C$_6$H$_4$)-C$_6$H$_4-$ | $-CCl_3$ |
| 4-(4-Cl-C$_6$H$_4$)-C$_6$H$_4-$ | $-CCl_2-CHCl-CH_3$ |
| 4-C$_6$H$_5$O-C$_6$H$_4-$ | $-CCl_3$ |
| 4-C$_6$H$_5$O-C$_6$H$_4-$ | $-CCl_2-CHCl-CH_3$ |
| 4-(4-Cl-C$_6$H$_4$-O)-C$_6$H$_4-$ | $-CCl_3$ |
| $CH_3O-C(CH_3)_2-$ | $-CCl_3$ |
| $CH_3O-C(CH_3)_2-$ | $-CCl_2-CHCl-CH_3$ |
| C$_6$H$_5-O-C(CH_3)_2-$ | $-CCl_3$ |
| C$_6$H$_5-O-C(CH_3)_2-$ | $-CCl_2-CHCl-CH_3$ |

The formula (III) provides a general definition of the acid halides also required for the preparation of the compounds according to the invention by process variant (a). In this formula, $R^5$ preferably represents those radicals which have already been mentioned as preferred in the case of the compounds of the formula (I).

The acid halides of the formula (III) are known, and they can be prepared by customary processes, for example by reacting carboxylic acids or alkali metal salts thereof with acid halides of phosphorus or sulphur. These methods are known from the general textbooks of organic chemistry.

The formula (IV) provides a general definition of the acid anhydrides furthermore required for the preparation of the compounds according to the invention by process variant (b). In this formula, $R^5$ preferably represents those radicals which have already been mentioned as preferred in the case of the compounds of the formula (I).

The acid anhydrides of the formula (IV) are known, and they can be prepared by known processes, for example by the action of acid chlorides on the alkali metal salts of the carboxylic acids. These processes are generally known.

The formula (V) provides a general definition of the isocyanates additionally required for the preparation of the substances according to the invention by process variant (c). In this formula, $R^8$ preferably represents alkyl with 1 to 4 carbon atoms or optionally substituted phenyl, preferred substituents being halogen, nitro, cyano, alkyl with 1 to 4 carbon atoms, alkoxy and alkylthio with in each case 1 or 2 carbon atoms and halogenoalkyl with up to 2 carbon atoms and up to 5 identical or different halogen atoms, such as, in particular, fluorine atoms and chlorine atoms.

The isocyanates of the formula (V) are known, and they can be prepared by processes which are generally customary and known, for example by reacting amines with phosgene and then heating the product.

Halogenating agents are also required for the preparation of the compounds according to the invention by process variant (d). Preferred halogenating agents which may be mentioned are inorganic acid halides, such as phosphorus trichloride, tribromide and pentachloride, phosphorus oxychloride, sulphonyl chloride and, in particular, thionyl chloride.

The formula (VI) provides a general definition of the (thio)alcoholates furthermore required for the preparation of the substances according to the invention by process variant (e). In this formula, $R^6$ preferably represents those radicals which have already been mentioned as preferred in the case of the compounds of the formula (I), and M preferably represents sodium, potassium or ammonium.

The starting substances of the formula (VI) are generally known compounds of organic chemistry.

The formula (VII) provides a general definition of the amines additionally required for the preparation of the substances according to the invention by process variant (f). In this formula, $R^9$ preferably represents hydrogen or alkyl with 1 to 4 carbon atoms. $R^{10}$ preferably represents alkyl with 1 to 4 carbon atoms or optionally substituted phenyl, preferred substituents being halogen, cyano, nitro and alkyl with 1 or 2 carbon atoms.

The starting compounds of the formula (VII) are generally known compounds of organic chemistry.

The formulae (VIII) and (IX) provide general definitions of the salts also required for the preparation of the compounds according to the invention by process variant (g). In these formulae, $R^5$ and $R^7$ preferably represent those radicals which have already been mentioned as preferred in the case of the compounds of the formula (I). M preferably represents those radicals which have already been mentioned as preferred in the case of the (thio)alcoholates of the formula (VI).

The starting substances of the formulae (VIII) and (IX) are generally known compounds of organic chemistry.

Preferred solvents for the reaction according to process variant (a) are inert organic solvents, especially amides, such as, in particular, dimethylformamide, and sulphoxides, such as, in particular, dimethylsulphoxide.

The reaction temperature can be varied within a substantial range in carrying out process variant (a). In general, the process is carried out at from 0° to 100° C., preferably from 20° to 85° C.

Process variant (a) can be carried out in the presence of an acid-binding agent (hydrogen halide acceptor) if appropriate; any of the customary acid-binding agents can be used here, especially organic bases, preferably tertiary amines, for example triethylamine, and pyridine or 4-dialkylaminopyridine, as well as inorganic bases, for example alkali metal carbonates.

Equimolar amounts of the reactants are preferably used in carrying out process variant (a). The compounds of the formula (I) may be isolated by customary methods.

Preferred solvents for the reaction according to process variant (b) are those which have already been mentioned in the case of process variant (a). Conveniently, an excess of the particular acid anhydride is employed.

Any of the customary acid catalysts, for example sulphuric acid, hydrogen chloride, hydrogen bromide, boron trifluoride and zinc chloride, can preferably be used as catalysts for process variant (b).

The reaction temperatures can be varied within a substantial range in carrying out process variant (b). In general, the process is carried out at from 0° to 150° C., preferably at from 80° to 120° C.

Equimolar amounts of the reactants are preferably used in carrying out process variant (b). For simplicity, the acid anhydride of the formula (IV) employed is also used as the solvent, whereupon an appropriate excess becomes necessary. Isolation of the compounds of the formula (I) is effected in the customary manner.

Preferred solvents for the reaction according to process variant (c) are those solvents which have already been mentioned in the case of process variant (a). Conveniently, an excess of the particular isocyanate can be employed.

Preferred catalysts which can be used in process variant (c) are tertiary bases, such as triethylamine and pyridine, or organo-tin compounds, such as dibutyl-tin dilaurate.

The reaction temperatures can be varied within a substantial range in carrying out process variant (c). In general, the process is carried out at from 0° to 100° C., preferably from 20° to 80° C.

Equimolar amounts of the reactants are preferably used in carrying out process variant (c). For simplicity, the isocyanate employed is used as the solvent, whereupon an appropriate excess becomes necessary. In order to isolate the compounds of the formula (I), the solvent is distilled off and the residue is worked up by customary methods.

Preferred solvents for the reaction according to process variant (d) are those solvents which have already been mentioned in the case of process variant (a). Conveniently, an excess of the particular inorganic acid halide used can be employed.

The reaction temperatures can be varied within a substantial range in carrying out process variant (d). In general, the process is carried out at from 0° to 100° C., preferably from 20° to 80° C.

Equimolar amounts of the reactants are preferably used in carrying out process variant (d). For simplicity, the halogenating agent employed is also used as the solvent, whereupon an appropriate excess becomes necessary. Isolation of the compound of the formula (I) is effected by a process in which the excess halogenating agent is removed, for example by distillation, aqueous sodium bicarbonate solution is added to the reaction mixture and the reaction product is extracted by shaking with an organic solvent.

Possible solvents for the reaction according to process variant (e) are all the inert organic solvents, especially ketones, such as diethyl ketone and, in particular, acetone, methyl isobutyl ketone and methyl ethyl ketone; alcohols, such as methanol, ethanol or isopropanol; nitriles, such as propionitrile and, in particular, acetonitrile; aromatic hydrocarbons, such as benzene, toluene or xylene; halogenated hydrocarbons, such as chloroform or methylene chloride; and formamides, such as, in particular, dimethylformamide.

The reaction temperatures can be varied within a substantial range in carrying out process variant (e). In general, the process is carried out at from 0° to 120° C., preferably from 20° to 100° C.

Equimolar amounts of the reactants are preferably used in carrying out process variant (e). In order to isolate the compound of the formula (I), the reaction mixture is filtered and the reaction product is isolated in the customary manner.

Possible solvents for the reaction according to process variant (f) are all the inert organic solvents, especially those solvents which have already been listed in the case of process variant (e).

Process variant (f) according to the invention is carried out in the presence of an acid-binding agent; any of the customary acid-binding agents can be used in this case, especially those substances which have already been mentioned in the case of process (a). However, an appropriate excess of amine of the formula (VII) can also be used.

The reaction temperatures can be varied within a substantial range in carrying out process variant (f). In general, the process is carried out at from 0° to 100° C., preferably at from 20° to 80° C.

Approximately equimolar amounts of the reactants are preferably used in carrying out process variant (f). In order to isolate the compound of the formula (I), the reaction mixture is filtered and the reaction product is isolated in the customary manner.

Preferred solvents for the reaction according to process variant (g) are organic acids, such as, in particular, glacial acetic acid, sulphonic acid and water-miscible inert organic solvents, such as ketones and alcohols.

The reaction temperatures can be varied within a substantial range in carrying out process variant (g). In general, the process is carried out at from 0° to 100° C., preferably from 20° to 80° C.

In carrying out process variant (g), 1 to 2 moles of a salt of the formula (VIII) or (IX) are generally employed per mole of the compound of the formula (Ia). Isolation of the compounds of the formula (I) is effected in the customary manner.

In a preferred embodiment of process variants (e) and (g), the procedure is appropriately to use as the starting material a (thio)alcohol in the case of process variant (e) and an acid derivative in the case of process variant (g), to convert the starting material into the (thio)alcoholate of the formula (VI) or, as appropriate, into the salt of the formulae (VIII) and (IX) in a suitable inert organic solvent and to react this product, without isolation, with a halide of the formula (Ia), whereupon the appropriate compound of the formula (I) according to the invention is obtained in one operation.

According to a further preferred embodiment, the reactions of process variants (e), (f) and (g) are carried out in a two-phase system, for example aqueous sodium hydroxide solution or potassium hydroxide solution/toluene or methylene chloride, 0.01 to 1 mole of a phase transfer catalyst, for example an ammonium compound or phosphonium compound, being added.

All the physiologically acceptable acids can be used for the preparation of acid addition salts of the compounds of the formula (I). Preferred acids include the hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid), and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII can preferably be used for the preparation of metal salt complexes of the compounds of the formula (I), example of metals which may be mentioned being copper, zinc, manganese, magnesium, tin, iron and nickel. Possible anions of the salts are those which are derived from physiologically acceptable acids, especially hydrogen halide acids, for example hydrochloric acid and hydrobromic acid, and phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds according to the invention have a broad spectrum of action and can be used against parasitic fungi which infect above-ground parts of plants or attack the plants through the soil, as well as against seed-borne pathogens. They develop a particularly good activity against parasitic fungi on above-ground parts of plants.

As plant protection agents, the active compounds according to the invention can be used with particularly good success for combating those fungi which cause powdery mildew diseases, for instance for combating Erysiphe species, for example the powdery mildew of cucumber causative organism (*Erysiphe cichoracearum* or the powdery mildew of barley or powdery mildew of cereal causative organism (*Erysiphe graminis*); or for combating those fungi which cause scab diseases; for instance for combating Venturia species, for example the apple scab causative organism (*Fusicladium dendriticum*). Good actions are also achieved against Pyricularia and Pellicularia in rice. It should be particularly emphasized that the active compounds according to the invention not only develop a protective action, but also have a systemic action. Thus, it is possible to protect plants against fungal attack when the active compound is fed to the above-ground parts of the plant via the soil and the root or via the seed.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering dry dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, active compound concentrations of 0.001 to 50 g, preferably 0.01 to 10 g, are generally employed per kilogram of seed.

For the treatment of soil, active compound concentrations of 0.00001 to 0.1% by weight, preferably 0.0001 to 0.02%, are generally employed at the place of action.

When used in appropriate concentrations, the substances according to the invention also exhibit acaricidal actions.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

(a) 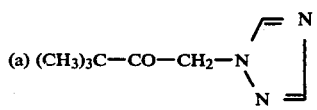

138 g (2 mol) of 1,2,4-triazole were added in portions to 276.4 g (2 mol) of ground potassium carbonate and 269.2 g (2 mol) of α-chloropinacolin in 500 ml of acetone at room temperature, whereupon the internal temperature rose to the boiling point. The mixture was stirred under reflux for 5 hours and then cooled to room temperature. The reaction mixture was filtered and the filtrate was concentrated by distilling off the solvent in vacuo. After adding benzine, the oily residue crystallised. 240.8 g (72% of theory) of 3,3-dimethyl-1-(1,2,4-triazol-1-yl)-butan-2-one of melting point 62°–64° C. were obtained.

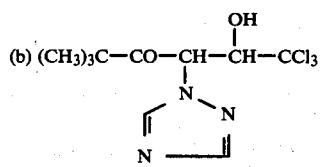

33.4 g (0.2 mol) of 3,3-dimethyl-1-(1,2,4-triazol-1-yl)-butan-2-one were dissolved in 150 ml of methylene chloride and the solution was cooled to −5° C. 19 g (0.1 mol) of titanium tetrachloride and then 29.5 g (0.2 mol) of chloral were slowly added dropwise to this solution. The internal temperature was maintained constant at −5° C. during the metering. Thereafter, the mixture was warmed slowly to the reflux and stirred for 3 hours. The reaction solution was poured onto ice and the white curdy precipitate which formed was filtered off. After boiling up the precipitate in 250 ml of methanol and then drying it, 19.9 g (32% of theory) of 1,1,1-trichloro-2-hydroxy-3-(1,2,4-triazol-1-yl)-5,5-dimethyl-hexan-4-one of melting point 220°–222° C. were obtained.

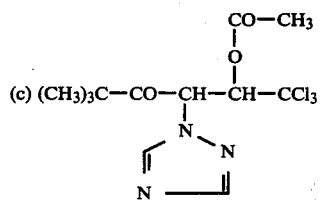

(i) Process variant (b)

314.6 g (1 mol) of 1,1,1-trichloro-2-hydroxy-3-(1,2,4-triazol-1-yl)-5,5-dimethyl-hexan-4-one were heated at 95° C. in 1,000 ml of acetic anhydride for 30 hours. The excess anhydride was then distilled off in vacuo, the residue was taken up in 750 ml of methylene chloride and the methylene chloride mixture was washed with 10% strength sodium bicarbonate solution until neutral. The organic phase was dried over sodium sulphate and concentrated by distilling off the solvent in vacuo. The residue was stirred with 150 ml of diisopropyl ether. 153.8 g (43% of theory) of 1,1,1-trichloro-2-acetoxy-3-(1,2,4-triazol-1-yl)-5,5-dimethyl-hexan-4-one were obtained as the pure diastereomer of the A* form of melting point 129°–131° C.

(ii) Process variant (a)

8.0 g (0.1 mol) of acetyl chloride were added to 31.5 g (0.1 mol) of 1,1,1-trichloro-2-hydroxy-3-(1,2,4-triazol-1-yl)-5,5-dimethyl-hexan-4-one in 100 ml of dimethylformamide at room temperature. Thereafter, the mixture was heated under reflux for 4 hours. It was left to cool and concentrated by distilling off the solvent in vacuo. The residue was taken up in methylene chloride and the methylene chloride solution was washed with aqueous sodium bicarbonate solution and dried over sodium sulphate. The solvent was distilled off and the residue was taken up in 100 ml of diisopropyl ether. After the diisopropyl ether mixture had stood for several hours, colorless crystals precipitated. 14.3 g (40% of theory) of 1,1,1-trichloro-2-acetoxy-3-(1,2,4-triazol-1-yl)-5,5-dimethylhexan-4-one were obtained as the pure diasteromer of the A* form of melting point 128°–130° C.

(iii) Process variant (g)

16.4 g (0.2 mol) of anhydrous sodium acetate were added to 31.5 g (0.1 mol) of 1,1,1,2-tetrachloro-3-(1,2,4-triazol-1-yl)-5,5-dimethyl-hexan-4-one in 150 ml of glacial acetic acid. The mixture was stirred at room temperature overnight and then heated to 40° C. for about 4 hours. The reaction mixture was then added to 1,000 ml of water and extracted twice with 250 ml of chloroform each time. The combined organic phases were dried over sodium sulphate and concentrated by distilling off the solvent in vacuo. The solid residue was recrystallized from ethanol and rinsed with a little hexane. 27.8 g (77.8% of theory) of 1,1,1-trichloro-2-acetoxy-3-(1,2,4-triazol-1-yl)-5,5-dimethylhexan-4-one were obtained as a diastereomer mixture of melting point 115°–119° C.

EXAMPLE 2

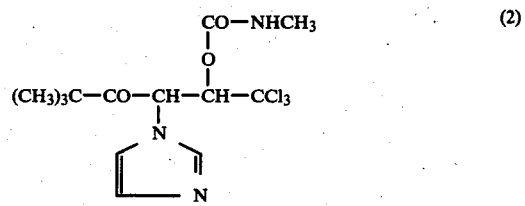

Process variant (c)

100 ml of methyl isocyanate were added to 15.8 g (0.05 mol) of 1,1,1-trichloro-2-hydroxy-3-(imidazol-1-yl)-5,5-dimethyl-hexan-4-one and the mixture was heated to 38° C. for 24 hours. The precipitate which had formed was filtered off and stirred with 200 ml of chloroform. The constituent which was insoluble in chloroform was the starting material and was filtered off. After distilling off the chloroform in vacuo, 6.9 g (44% of theory, relative to the starting material actually consumed) of 1,1,1-trichloro-2-methylcarbamoyloxy-3-(imidazol-1-yl)-5,5-dimethyl-hexan-4-one of melting point 104°–108° C. were obtained.

EXAMPLE 3

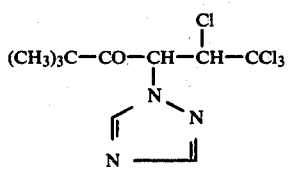 (3)

Process variant (d)

393.3 g (1.25 mol) of 1,1,1-trichloro-2-hydroxy-3-(1,2,4-triazol-1-yl)-5,5-dimethyl-hexan-4-one were introduced into 750 ml of thionyl chloride, while stirring, and the mixture was heated to 60° C. for 36 hours. Thereafter, the excess thionyl chloride was distilled off in vacuo. The residue was taken up in 1.5 liters of methylene chloride and the methylene chloride mixture was washed with 10% strength sodium bicarbonate solution until neutral, dried over sodium sulphate and concentrated by distilling off the solvent in vacuo. 408.9 g (98% of theory) of 1,1,1,2-tetrachloro-3-(1,2,4-triazol-1-yl)-5,5-dimethyl-hexan-4-one of melting point 111°–113° C. were obtained.

EXAMPLE 4

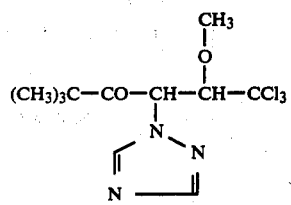 (4)

Process variant (e)

A solution of 5.4 g (0.1 mol) of sodium methylate in 50 ml of absolute methanol was added to a solution of 33.3 g (0.1 mol) of 1,1,1,2-tetrachloro-3-(1,2,4-triazol-1-yl)-5,5-dimethyl-hexan-4-one (Example 3) in 150 ml of absolute methanol. The mixture was subsequently stirred at 60° C. for 5 hours, the sodium chloride which had precipitated was filtered off and the filtrate was concentrated by distilling off the solvent in vacuo. The residue was taken up in 150 ml of methylene chloride, and the methylene chloride mixture was washed twice with 150 ml of water each time, dried over sodium sulphate and concentrated. The partially crystalline residue was stirred in 250 ml of diisopropyl ether, whereupon it crystallized completely. After recrystallization from isopropanol, 18.8 g (57% of theory) of 1,1,1-trichloro-2-methoxy-3-(1,2,4-triazol-1-yl)-5,5-dimethyl-hexan-4-one of melting point 93°–96° C. were obtained.

EXAMPLE 5

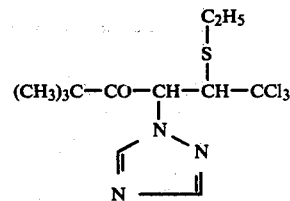 (5)

Process variant (e)

3.1 g (0.05 mol) of ethylmercaptan were added dropwise to a solution of 3.4 g (0.05 mol) of sodium methylate in 50 ml of absolute ethanol. The mixture was subsequently stirred at room temperature for 1 hour. A solution of 16.7 g of 1,1,1,2-tetrachloro-3-(1,2,4-triazol-1-yl)-5,5-dimethyl-hexan-4-one (Example 3) in 200 ml of ethanol was then added dropwise to this mixture, and the resulting mixture was subsequently stirred at room temperature for 6 hours. The inorganic salt was then filtered off and the filtrate was concentrated. After triturating in hexane, the residue crystallized. 8.9 g (50% of theory) of 1,1,1-trichloro-2-ethylmercapto-3-(1,2,4-triazol-1-yl)-5,5-dimethyl-hexan-4-one of melting point 101°–105° C. were obtained.

EXAMPLE 6

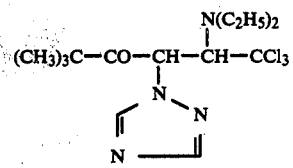 (6)

Process variant (f)

14.6 g (0.2 mol) of diethylamine were slowly added dropwise to 33.4 g (0.1 mol) of 1,1,1,2-tetrachloro-3-(1,2,4-triazol-1-yl)-5,5-dimethyl-hexan-4-one (Example 3) in 150 ml of tetrahydrofuran at room temperature. The mixture was then subsequently stirred at 50°–60° C. for 3 hours. The diethylamine hydrochloride which had precipitated was filtered off and the filtrate was concentrated in vacuo. According to thin layer chromatography of the residue over silica gel 60 (Merck, particle size 0.063–0.200 mm) and with ether/hexane in the ratio 1:1 as the running agent, 1,1,1-trichloro-2-diethylamino-3-(1,2,4-triazol-1-yl)-5,5-dimethyl-hexan-4-one was obtained as the pure diastereomer of the A* form, as a yellow oil, in a yield of 8.9 g (24.1% of theory), and as the pure diastereomer of the B* form, of melting point 103°–110° C., in a yield of 6.4 g (19.4% of theory).

*A and B forms = in each case one of the two possible isomers.

The following compounds of the general formula

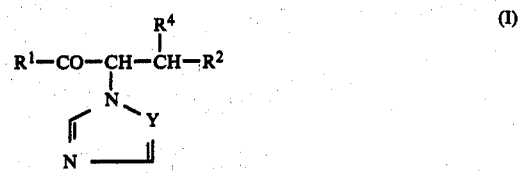 (I)

were obtained in a corresponding manner:

TABLE 3

| Compound No. | R¹ | R² | R⁴ | Y | Melting point (°C.) |
|---|---|---|---|---|---|
| 7 | $(CH_3)_3C-$ | $-CCl_3$ | $-O-CO-C_2H_5$ | N | 115-17 |
| 8 | $(CH_3)_3C-$ | $-CCl_3$ | $-O-CO-C_3H_7-n$ | N | 106-08 |
| 9 | $(CH_3)_3C-$ | $-CCl_3$ | $-O-CO-NHCH_3$ | N | 151-55 |
| 10 | $(CH_3)_3C-$ | $-CCl_3$ | $-O-C_2H_5$ | N | 100-04 |
| 11 | $(CH_3)_3C-$ | $-CCl_3$ | $-O-\phi-Cl$ | N | 163-65 |
| 12 | $(CH_3)_3C-$ | $-CCl_3$ | $-NH-C_3H_7-n$ | N | 92-95 |
| 13 | $(CH_3)_3C-$ | $-CCl_3$ | $-O-CO-CH(CH_3)_2$ | N | 93-102 |
| 14 | $(CH_3)_3C-$ | $-CCl_3$ | $-O-CO-NH-\phi$ | N | 166-75 |
| 15 | $(CH_3)_3C-$ | $-CCl_3$ | $-S-\phi$ | N | 163-69 |
| 16 | $\phi-$ | $-CCl_3$ | $-O-CO-NHCH_3$ | CH | 113-17 |
| 17 | $(CH_3)_3C-$ | $-CCl_3$ | $-O-CO-CH_3$ | N | 226-27 (× CuCl₂) |
| 18 | $(CH_3)_3C-$ | $-CCl_3$ | $-O-CO-NHCH_3$ | N | 217-19 (× CuCl₂, A-Form) |
| 19 | $(CH_3)_3C-$ | $-CCl_3$ | $-O-CO-NHCH_3$ | N | 230 decomposition (× CuCl₂, B-Form) |
| 20 | $ClCH_2-C(CH_3)_2-$ | $-CCl_3$ | $-O-CO-CH_3$ | N | 78-81 |
| 21 | $(CH_3)_3C-$ | $-CCl_3$ | Cl | N | 202-03 (× CuCl₂) |
| 22 | $\phi-$ | $-CO-O-C_2H_5$ | $-O-CO-NHCH_3$ | CH | Oil |
| 23 | $(CH_3)_3C-$ | $-CCl_3$ | $-O-CO-NH-\phi$ | N | 180-82 (× CuCl₂, A-form) |
| 24 | $(CH_3)_3C-$ | $-CCl_3$ | $-O-CO-NH-\phi$ | N | 150-58 (× CuCl₂, B-form) |
| 25 | $(CH_3)_3C-$ | $-CCl_2-CHCl-CH_3$ | $-O-CO-CH_3$ | N | 171-74 |
| 26 | $(CH_3)_3C-$ | $CF_3$ | $-O-CO-CH_3$ | N | 70-79 |
| 27 | $(CH_3)_3C-$ | $-CHCl_2$ | $-O-CO-CH_3$ | N | 109-11 |
| 28 | $FCH_2-C(CH_3)_2-$ | $-CCl_3$ | $-O-CO-CH_3$ | N | 102-04 |
| 29 | $ClCH_2-C(CH_3)_2-$ | $-CCl_3$ | $-O-CO-CH_3$ | N | 78-81 |
| 30 | $(CH_3)_3C-$ | $-CCl_2-CHCl-CH_3$ | $-O-CO-NHCH_3$ | N | 114-15 |
| 31 | $FCH_2-C(CH_3)_2-$ | $-CCl_3$ | $-O-CO-NHCH_3$ | N | 128-29 |
| 32 | $ClCH_2-C(CH_3)_2-$ | $-CCl_3$ | $-O-CO-NHCH_3$ | N | 140-41 |
| 33 | $(CH_3)_3C-$ | $-CHCl_2$ | $-O-CO-NHCH_3$ | N | 159-60 |
| 34 | $(CH_3)_3C-$ | $-CCl_2-CHCl-CH_3$ | Cl | N | oil |
| 35 | $Cl-\phi-$ | $-CCl_3$ | Cl | N | 156-70 (× HCl) |
| 36 | $(CH_3)_3C-$ | $-CCl_2-CH_2Cl$ | $-O-CO-CH_3$ | N | 102-10 |
| 37 | $CH_3-SO_2-O-CH_2-C(CH_3)_2-$ | $-CCl_3$ | $-O-CO-CH_3$ | N | 155-57 |
| 38 | $(CH_3)_3C-$ | $-CCl_2-CH_2Cl$ | $-O-CO-NHCH_3$ | N | 113-15 |

The fungicidal activity of the compounds of this invention is illustrated by the following examples wherein the compounds according to the present invention are each identified by the number (given in brackets) from Examples 1 to 6 and Table 3:

EXAMPLE 7

Erysiphe test (cucumber)/systemic
Solvent: 4.7 parts by weight of acetone
Emulsifier: 0.3 part by weight of alkylaryl polyglycol ether
Water: 95 parts by weight The amount of active compound required to give the desired concentration of active compound in the watering liquid was mixed with the stated amount of solvent and the concentrate was diluted with the stated amount of water which contained the stated amount of emulsifier.

Cucumber plants grown in standard soil, in the 1-2 leaf stage, were watered three times within one week with 10 ml of the watering liquid, of the stated concentration of active compound, per 100 ml of soil.

The plants treated in this way were inoculated, after treatment, with conidia of the fungus *Erysiphe cichoracearum*. The plants were then set up in a greenhouse at 23-24 degrees C. and 70% relative atmospheric humidity. After 12 days, the infection of the cucumber plants were determined. The assessment data were converted to percent infection. 0% denoted no infection and 100% denoted that the plants were completely infected.

In this test, for example, the following compounds exhibited a very good action, which was superior to that of the compounds known from the prior art: (1), (7), (8), (3), (4) and (10).

EXAMPLE 8

Fusicladium test (apple)/systemic
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Apple seedlings grown in standard soil, in the 3 to 4 leaf stage, were watered once within one week with 10 ml of the watering liquid, of the stated concentration of active compound, per 100 ml of soil.

The plants treated in this way were inoculated, after treatment, with an aqueous conidia suspension of *Fusicladium dentriticum* and incubated for 18 hours in a humidity chamber at 18-20 degrees C. and at a relative atmospheric humidity of 100%.

The plants were then brought into a greenhouse again for 14 days.

15 days after inoculation, the infection of the seedlings was determined. The assessment data were converted to percent infection. 0% meant no infection; 100% meant that the plants were totally infected.

In this test, for example, the following compounds exhibited a very good action, which was superior to that of the compounds known from the prior art: (1), (7), (8), (3), (4), (10), (9) and (6).

EXAMPLE 9

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether, 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21-22 deg. C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

In this test, for example, the following compounds exhibited a very good action, which was superior to that of the compounds known from the prior art: (1), (7), (8), (3) and (10).

EXAMPLE 10

Powdery mildew of barley (*Erysiphe graminis* var. *hordei*) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. *hordie* and grown on at 21-22 deg. C. and 80-90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The active compound was the more active, the lower was the degree of mildew infection.

In this test, for example, the following compounds exhibited a very good action, which was superior to that of the compounds known from the prior art: (1), (3) and (4).

It will be appreciated that the instant specification and examples are set forth by way of illustration and not limitation, and that various modifications and changes may be made without departing from the spirit and scope of the present invention.

We claim:

1. An α-azolyl-keto derivative of the formula $$R^1-CO-CH-\underset{\underset{N}{|}}{\overset{\overset{R^4}{|}}{CH}}-R^2$$

$$\underset{N \longrightarrow}{\overset{\diagup}{\underset{\|}{\bigg\|}}} \overset{\diagdown}{\underset{Y}{\bigg\|}}$$

in which
R$^1$ represents C$_{1-4}$-alkyl; C$_{1-4}$-alkyl substituted by at least one substituent selected from the group consisting of halogen, C$_{1-4}$-alkylcarbonyloxy, optionally substituted phenylcarbonyloxy, C$_{1-4}$-alkyl- or dialkylcarbamoyloxy, C$_{1-4}$-alkylsulphonyloxy, optionally substituted phenylsulphonyloxy, C$_{1-4}$-dialkylaminosulphonyloxy, C$_{1-4}$-alkoxy and optionally substituted phenoxy wherein aforementioned optional substituents are selected from the group consisting of halogen, cyano, nitro, C$_{1-4}$-alkyl, C$_{5-7}$-cycloalkyl, halogenomethyl, halogenoethyl, and phenyl, phenoxy or benzyl, the last three radicals optionally being substituted by halogen, cyano or nitro;

$R^2$ represents the grouping $-CX^1X^2R^3$ or $C_{1-4}$-alkoxycarbonyl;

$R^3$ represents halogen, halogeno-$C_{1-4}$-alkyl, phenyl, halogenophenyl, methylphenyl, ethylphenyl, halogenomethylphenyl, halogenoethylphenyl, cyanophenyl or nitrophenyl;

$R^4$ represents the grouping $-O-R^6, -S-R^6, -O-SO-R^7$, $$-O-\overset{O}{\underset{\|}{C}}-NHCH_3,$$

halogen, $C_{1-4}$-alkyl- or dialkyl-amino, phenylamino, halogenophenylamino, cyanophenylamino, nitrophenylamino, methylphenylamino or ethylphenylamino $R^6$ represents $C_{1-4}$-alkyl, $C_{2-4}$-alkenyl or alkynyl, $C_{5-7}$-cycloalkyl, phenyl, benzyl, phenyl or benzyl substituted with halogen, nitro, cyano, $C_{1-4}$-alkyl, methoxy, ethoxy, methylthio, ethylthio, halogenomethyl or halogenoethyl;

$R^7$ represents $C_{1-4}$-alkyl, $C_{1-4}$-dialkylamino, phenyl, phenyl substituted by chlorine, bromine or methyl, or halogeno-$C_{1-4}$-alkyl with up to 5 halogen atoms;

$X^1$ and $X^2$ each independently represents hydrogen, fluorine chlorine or bromine; and Y is a nitrogen atom or the CH group;

or an addition salt thereof with an acid selected from the group consisting of a hydrogen-halide acid, phosphoric acid, nitric acid, sulphuric acid a carboxylic acid and a sulphonic acid, or a metal salt complex thereof, the metal of the salt being selected from main groups II to IV and sub-groups I, II and IV to VIII of the Periodic Table and the anion of the salt being derived from a hydrogen halide acid, sulphuric acid, nitric acid or phosphoric acid.

2. A compound or salt or complex thereof according to claim 1, in which said compound is 1,1,1,2-tetrachloro-3-(1,2,4-triazol-1-yl)-5,5-dimethyl-hexan-4-one of the formula

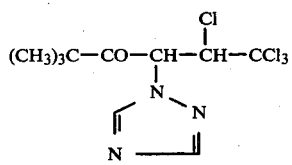

3. A compound or salt or complex thereof according to claim 1, in which said compound is 1,1,1-trichloro-2-methoxy-2-(1,2,4-triazol-1-yl-5,5-dimethyl-hexan-4-one of the formula

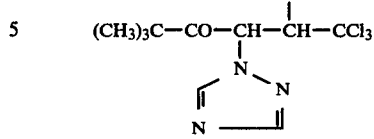

4. A compound or salt or complex thereof according to claim 1, in which said compound is 1,1,1-trichloro-2-diethylamino-3-(1,2,4-triazol-1-yl)-5,5-dimethyl-hexan-4-one of the formula

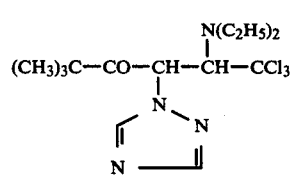

5. A compound or salt or complex thereof according to claim 1, in which said compound is 1,1,1-trichloro-2-methylcarbamoyloxy-3-(1,2,4-triazol-1-yl)-5,5-dimethylhexan-4-one of the formula

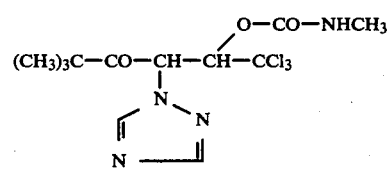

6. A compound or salt or complex thereof according to claim 1, in which said compound is 1,1,1-trichloro-2-ethoxy-3-(1,2,4-triazol-1-yl)-5,5-dimethyl-hexan-4-one of the formula

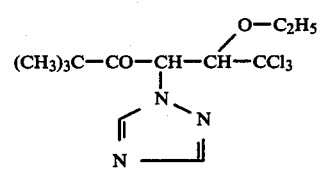

7. A fungicidal composition containing as active ingredient a fungicidally effective amount of a compound according to claim 1 in admixture with a diluent.

8. A method of combating fungi which comprises applying to the fungi, or to a habitat thereof, a fungicidally effective amount of a compound according to claim 1.

9. The method according to claim 8 in which said compound is
1,1,1,2-tetrachloro-3-(1,2,4-triazol-1-yl)-5,5-dimethyl-hexan-4-one,
1,1,1-trichloro-2-methoxy-3-(1,2,4-triazol-1-yl)-5,5-dimethyl-hexan-4-one,
1,1,1-trichloro-2-diethylamino-3-(1,2,4-triazol-1-yl)-5,5-dimethyl-hexan-4-one,
1,1,1-trichloro-2-methylcarbamoyloxy-3-(1,2,4-triazol-1-yl)-5,5-dimethyl-hexan-4-one, or
a compound or salt or complex thereof or a physiologically acceptable acid addition salt or metal salt complex thereof.